United States Patent [19]

Clark, III

[11] Patent Number: 4,700,451

[45] Date of Patent: Oct. 20, 1987

[54] METHOD FOR AUTOMATICALLY INDEXING CAST FIELD SHAPING BLOCKS TO A RADIATION THERAPY TREATMENT TRAY AND A COOLING TRAY FOR CAST BLOCKS

[76] Inventor: William T. Clark, III, 13 Park La., Folsom, La. 70437

[21] Appl. No.: 862,969

[22] Filed: May 14, 1986

Related U.S. Application Data

[62] Division of Ser. No. 658,434, Oct. 5, 1984, abandoned.

[51] Int. Cl.⁴ .............................................. B23P 17/00
[52] U.S. Cl. .................................... 29/527.5; 29/407; 164/6; 378/68; 378/140; 250/515.1
[58] Field of Search .................... 29/527.5, 407; 164/6, 164/47, 137, 339, 341, 412; 604/20; 378/64, 65, 68, 140, 154, 156, 157, 158, 159, 160, 161, 210; 250/515.1

[56] References Cited

U.S. PATENT DOCUMENTS 3,826,301 7/1974 Brooks ........................... 29/527.5 X
3,937,971 2/1976 Morrison et al. ............ 250/515.1 X Primary Examiner—Howard N. Goldberg
Assistant Examiner—Ronald S. Wallace
Attorney, Agent, or Firm—Nies, Webner, Kurz & Bergert

[57] ABSTRACT

A method is described for indexing a polyfoam block in which a metal field shaping block is cast to both the cutting tray of a hot wire cutting system and the treatment tray of a radiation therapy treatment machine. The cast metal field shaping block is automatically correctly oriented for treatment. A cooling tray for cooling the casting is also described.

5 Claims, 5 Drawing Figures

METHOD FOR AUTOMATICALLY INDEXING CAST FIELD SHAPING BLOCKS TO A RADIATION THERAPY TREATMENT TRAY AND A COOLING TRAY FOR CAST BLOCKS

This is a division of application Ser. No. 658,434 filed Oct. 5, 1984, now abandoned.

BACKGROUND OF THE INVENTION

It is conventional practice in radiation therapy to cast beam-forming field shaping blocks specifically individualized to each patient. The eutectic alloy field shaping blocks are usually cast in a polyfoam block such as polystyrene which has been especially cut to make the mold. One method of cutting the field shaping block molds is to place the patient X-ray a set distance from a pivot which simulates the radiation source and to place a block of rigid polyfoam a set distance between the X-ray and the pivot and to cut the polyfoam with a hot wire cutter which follows either a pivoted rigid rod or a long wire cable as the operator traces the outline of the designated treatment areas on the X-ray.

The voids thus created in the polyfoam are then filled with a molten eutectic alloy which cools to become one or more field shaping blocks. The blocks are then placed on a treatment tray in the beam of the radiation therapy machine, such as an accelerator or cobalt unit. The field shaping blocks are manipulated into position on the treatment tray to shield the areas of the patient which are to be protected from radiation.

While this current practice of defining the radiation beam is certainly better than the older practice of simply arranging rectangular lead blocks on the treatment tray, the whole process leaves much to be desired, and it leads to many cumulative inaccuracies because the process described above cannot orient field shaping blocks with sufficient accuracy for use with modern high-powered, well-collimated treatment machines. Even slight errors in orientation can seriously undermine the physician's intent by allowing some areas to go untreated while others are seriously over-exposed. Furthermore, in casting the blocks, conventional cooling trays do not provide uniform pressure in holding the polyfoam block, and they permit spillage to occur.

Accordingly, it is an object of this invention to provide an improved system of indexing and orienting accurately formed cast field shaping blocks in radiotherapy treatment apparatus. It is another object to provide a cooling tray for cast field shaping blocks.

DESCRIPTION OF THE INVENTION

The invention provides an indexing system which automatically ensures correct placement of the field shaping eutectic alloy block in the radiotherapy treatment machine in a position exactly analogous to that of the cavity in which the field shaping block was cut from the styrofoam block in the hot wire cutting machine using, advantageously, the hot wire cutting system described in my copending patent application, Ser. No 658,435, filed Oct. 5, 1984, now U.S. Pat. No. 4,601,224 issued July 22, 1986.

Unless the the cast alloy shielding blocks are correctly situated upon the treatment tray, all the accuracy in cutting has been wasted. It is therefore paramount to orient the shielding blocks in the correct position on the radiation treatment tray. Accordingly, it is a purpose of this invention to index the polyfoam block to the cutting tray used in the cutting system and to the treatment tray used in the treatment machine in such manner that the shielding blocks cast within the polyfoam block will automatically be correctly oriented on the treatment tray. The shielding blocks can be fastened to the tray in correct position before the polyfoam is removed.

A method is described of indexing to a treatment tray used in a radiation therapy treatment machine having a radiation source and a patient positioned for treatment in line with the radiation source, a polyfoam block having a cavity cut in it by cutting apparatus having a phantom radiation source and a patient X-ray film positioned in line with the phantom source, the cavity being filled with a cast metal field shaping block. The polyfoam block containing the cast metal field shaping block is indexed to the treatment tray of the radiation therapy treatment machine with respect to the radiation source and positioned patient identically to the indexation of the polyfoam block to a block support or cutting tray in the cutting apparatus with respect to the phantom radiation source and patient X-ray film. The polyfoam block may be indexed to the treatment tray by an arrangement of fasteners, the arrangement of fasteners being identical to an arrangement of fasteners fastening the polyfoam block to the block support or cutting tray in the cutting apparatus.

A polyfoam block such as polystyrene foam is used for cutting the cavities in which the shielding blocks used in radiation therapy are cast because it has a high degree of dimensional stability. An indexing method which capitalizes upon this stability and rigidity is desirable. Accordingly, a convenient method to index the polyfoam block to the cutting machine tray and the treatment machine tray is to deform an unused area of the polyfoam block in such manner that the polyfoam block will index to the cutter tray and to the treatment tray by interlock to the deformation.

Any of several practical and simple arrangements are suitable for this "lock and key" index system. For example, both the cutter tray and the treatment tray may have a series of raised pins which indent the polyfoam, thus assuring precise location. Alternatively, the arrangement of FIGS. 1-5, in which like parts are similarly numbered, offers the advantage of increased mechanical stability because it holds the foam block firmly in place.

Figure 1:
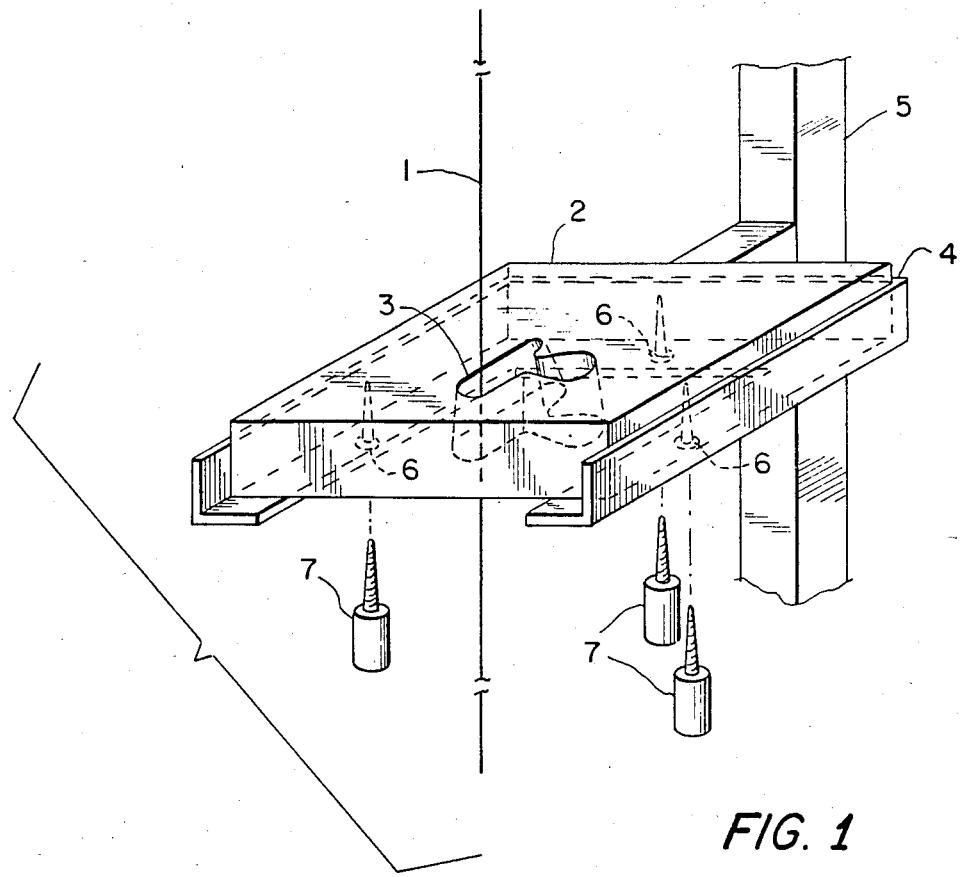
FIG. 1 shows a partially exploded supporting system for indexing the polyfoam block to the cutting machine tray.

In FIG. 1 there is shown vertical column 5 supporting a cutter tray 4 which holds a block of polyfoam 2 shown with a cut pattern forming a cavity 3 and cutter wire 1. The polyfoam block 2 is held in the tray with two or more thumb screws 7 which pass into the polyfoam block 2 through holes 6 in the cutter tray 4.

The dimensional stability of the rigid polyfoam makes it ideal for molding and indexing the shielding blocks. However, because the polyfoam is lightweight, inelastic, and easily crushed or deformed, it has long presented great difficulties in the casting process itself.

While the polyfoam is light in weight, the eutectic alloy is very heavy, approximating the weight of lead. It is consequently necessary to hold the polyfoam mold firmly against a cooling surface while the molten alloy is poured into the cavity in the polyfoam or the alloy will displace the polyfoam, spill out, and spoil the casting. While various clamps and weights have previously been devised to immobilize the polyfoam, none have proven truly satisfactory, because either they crush the polyfoam, or they do not maintain the polyfoam in uniform, intimate contact with the cooling surface. The conventional method is to tape shut the "closed" end of the mold cavity. This method not only wastes time, but it also greatly retards cooling.

In order to eliminate these problems, it is essential to provide uniform pressure on the polYfoam so that the casting is not distorted, yet the pressure must be sufficient to intimately immobilize the polyfoam block against the cooling surface. Furthermore, the cooling surface must conduct heat rapidly and efficiently so that the eutectic alloy solidifies rapidly and forms its own seal as the remainder of the alloy is poured.

A cooling tray of this invention for cooling a field shaping block cast in a cavity in a polyfoam block comprises a generally flat heat-sink base means for supporting the polyfoam block on an upper surface thereof, a spaced pair of clamp support means affixed on the cooling tray for embracing respectively opposite sides of the polyfoam block disposed in the space therebetween, a pair of angle clamps each comprising first and second flanges disposed at right angles to one another, hinges pivotly supporting the first flanges of the angle clamps on the clamp support means with the second flanges thereof disposed over the space between the clamp support means, and spring means for biasing the angle clamps to pivot about the hinges and normally biasing the angle clamps to pivot so that the second flanges thereof are forced downwardly toward the space between the clamp support means, whereby to force the second flanges downwardly against the polyfoam block supported on the tray between the clamp support means.

Figure 2:
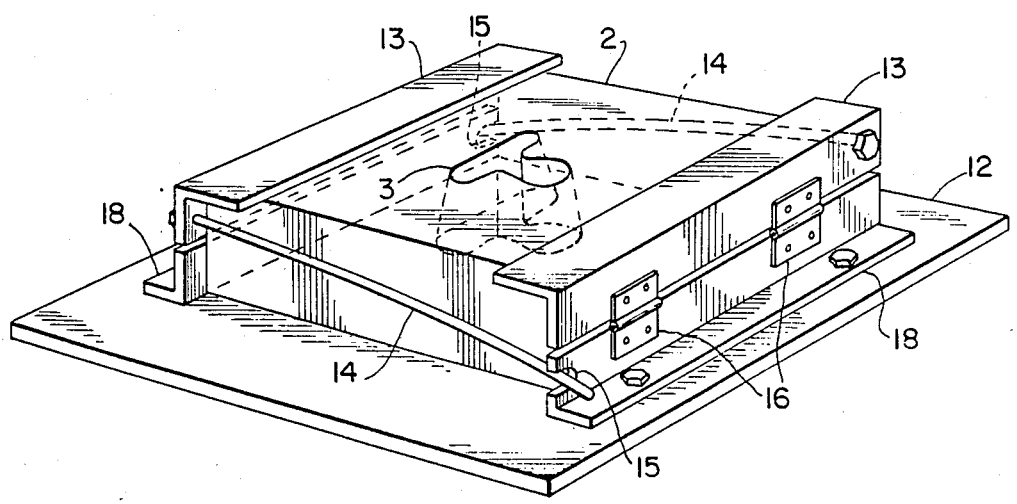
FIG. 2 shows a tray suitable for pouring and cooling a cast metal shielding block.

FIG. 2 shows a cooling tray 12 which holds the polyfoam block 2 while the metal casting is poured and cooled. The cooling tray 12 has a heat-sink cooling surface such as brushed or etched aluminum, and is shown with a block of polyfoam 2 immobilized upon it by means of two or more angle clamps 13. Angle clamps 13 seize polyfoam block 2 along its edges and distribute clamping pressure uniformly without distortion. Clamps 13 rotate to exert even pressure by means of long springs 14 connected to angle clamps 13. The free ends of springs 14 fit into slots 15 in the opposite angle clamps 13 or clamp supports 18 which are rigidly attached to cooling tray 12 and hinged with hinges 16 to angle clamps 13. Springs 14 provide great mechanical advantage for ease of operation and high, exactly reproducible clamping pressure, while the geometry of the rotating angle clamps 13 resists twisting and uneven pressure, unlike conventional screw or lever clamps.

With the polyfoam molding block 2 thus securely immobilized, it is necessary to cool the eutectic alloy as rapidly and efficiently as possible so that the alloy becomes "self-sealing" and cannot leak out of the lower "closed" end of the cavity 3 in the polyfoam block 2 which rests upon the cooling surface of tray 12. Accordingly, the surface of the cooling heat-sink tray 12 should be brushed or etched in order to increase surface area and improve thermal transfer. When the alloy is poured into cavity 3 the alloy begins to solidify instantly and provides its own seal. Castings can thereby be produced very rapidly with little difficulty, and cooling time can be reduced from hours to minutes.

Figure 3:
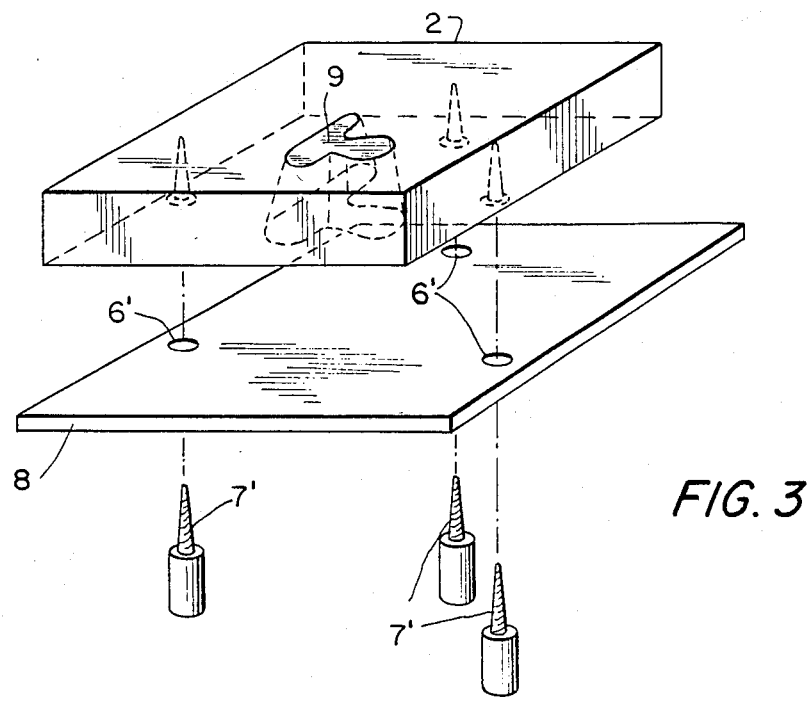
FIG. 3 shows an exploded view of an indexing system for securing the polyfoam block on the treatment tray.

In FIG. 3 the polyfoam block 2 with the metal casting 9 in place is shown ready for attachment to the treatment tray 8 by means of fasteners, shown as thumb screws 7', which pass through holes 6' in treatment tray 8.

Figure 4:
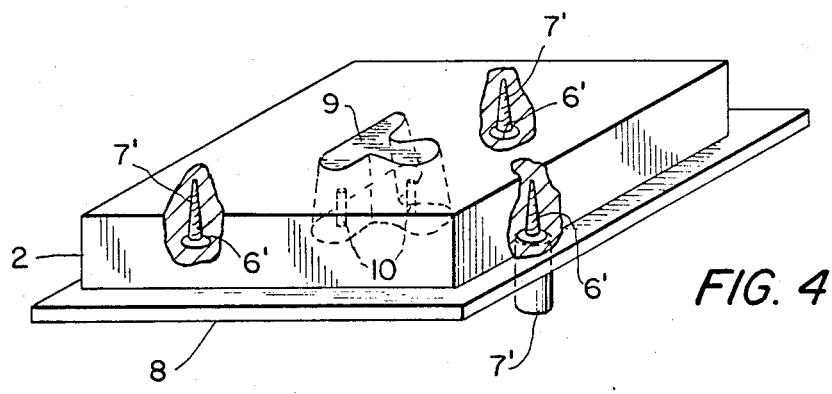
FIG. 4 shows a secured metal block cast in a secured polyfoam block on the treatment tray.

FIG. 4 shows the polyfoam block 2 in place on the treatment tray 8, fastened by thumb screws 7' through holes 6' in the treatment tray. The holes 6' in the treatment tray 8 are situated identically to the holes 6 in the cutter tray shown in FIG. 1. The cut cavity is shown already cast with the eutectic alloy casting 9 which has been attached to the treatment tray 8 by means of the screws 10.

Figure 5:
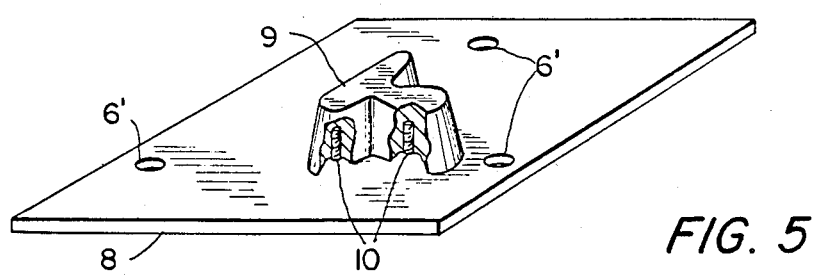
FIG. 5 shows a partially cut away cast metal block secured to the treatment tray.

FIG. 5 shows the treatment tray 8 with the polyfoam block removed and the casting 9 left in correct location by means of screws 10. The now unused indexing holes 6' are shown for clarity.

Of course, many such mechanical indexing arrangements are possible, but the essential feature is that the polyfoam block must index to both the cutter tray and the treatment tray in such manner that the cast field shaping block will occupy the same location on both trays. In the illustrated example, this was done with an identical pattern of holes and screws in both the cutter and treatment trays; the pattern is thus located and the field shaping blocks oriented with perfect accuracy. In this manner the relationship between the hot wire pivot position (phantom radiation source), the cut polyfoam block on the cutting tray and the patient X-ray film, in a hot wire cutting system, is identical to the relationship between the radiation source, the cast metal field shaping block on the treatment tray and the patient during treatment using a radiation therapy treatment machine.

In use, the treatment machine operator slides the cast metal block secured to the treatment tray into the treatment machine and the metal block then needs no further manipulation to ensure proper orientation or placement for treatment because the polyfoam block into which the metal block was cast was identically indexed to both the cutting and treatment trays.

For some procedures it is necessary to use a cast block of paraffin or other material rather than the cast eutectic alloy (or other cast metal) block. The apparatus and method described above are suitable for casting and use of paraffin blocks as well as for metal blocks.

Variations and modifications of this invention can be effected within the spirit and scope of the invention as described above and as defined in the appended claims.

I claim:

1. A method of indexing a field shaping block to a treatment tray used in a radiation therapy treatment machine, which machine has a radiation source and means for supporting a patient positioned for treatment in line with said source, cutting in a polyfoam block a cavity by cutting apparatus which has a phantom radiation source and a patient X-ray film positioned in line with said phantom source, casting on said cavity a metal field shaping block, indexing said polyfoam block containing the cast metal field shaping block to the treatment tray of the radiation therapy treatment machine and positioning the patient identically to the indexation of said polyfoam block to a block support in said cutting apparatus with respect to the phantom radiation source and patient X-ray film.

2. A method of indexing of claim 1 wherein said polyfoam block is indexed to said treatment tray by an arrangement of fasteners, said arrangement being identical to an arrangement of fasteners fastening said polyfoam block to said block support in said cutting apparatus.

3. A method for indexing field shaping blocks to a radiation therapy treatment tray comprising:

supporting a polyfoam block to be cut by a hot wire cutting system, indexing the polyfoam block to its support in the cutting system, cutting the supported, indexed polyfoam block with the hot wire to form a cavity in the polyfoam block, securing the cut polyfoam block on a cooling tray, pouring molten metal into the cavity in the polyfoam block secured to the cooling tray, cooling the molten metal to form a cast metal block, positioning the polyfoam block having the metal block cast into the cavity on the treatment tray of the radiation therapy treatment machine, in an indexed position wherein the polyfoam block is indexed to the treatment tray of the radiation therapy treatment machine with respect to its radiation source and positioned patient identically to the indexation of said polyfoam block to the block support in the hot wire cutting system with respect to its radiation source and patient X-ray film, securing the cast metal block to the treatment tray in its indexed position.

4. A method of claim 3 further comprising removing the polyfoam block from its indexed position surrounding the cast metal block secured on the treatment tray.

5. A method of claim 3 wherein the cut polyfoam block is secured to the cooling tray by means of spring-held angle-clamps.

* * * * *

REEXAMINATION CERTIFICATE (2974th)
United States Patent [19]
Clark, III

[11] B1 4,700,451
[45] Certificate Issued Aug. 20, 1996

[54] METHOD FOR AUTOMATICALLY INDEXING CAST FIELD SHAPING BLOCKS TO A RADIATION THERAPY TREATMENT TRAY AND A COOLING TRAY FOR CAST BLOCKS

[76] Inventor: William T. Clark, III, 13 Park La., Folsom, La. 70437

Reexamination Request:
No. 90/003,923, Aug. 15, 1995

Reexamination Certificate for:
Patent No.: 4,700,451
Issued: Oct. 20, 1987
Appl. No.: 862,969
Filed: May 14, 1986

Related U.S. Application Data

[62] Division of Ser. No. 658,434, Oct. 5, 1984, abandoned.
[51] Int. Cl.$^6$ .................................................. B23P 17/00
[52] U.S. Cl. ........................... 29/527.5; 164/6; 250/515.1; 378/68; 378/140

[56] References Cited

U.S. PATENT DOCUMENTS

| | | |
|---|---|---|
| 595,267 | 12/1897 | MacHarg . |
| 695,507 | 3/1902 | Strang . |
| 2,183,790 | 12/1939 | Dillehay et al. . |
| 2,405,444 | 8/1946 | Moreau et al. . |
| 3,718,310 | 2/1973 | Cerone . |
| 3,826,301 | 7/1974 | Brooks . |
| 3,937,971 | 2/1976 | Morrison et al. . |
| 3,968,711 | 7/1976 | Wilson ................................ 83/171 |

FOREIGN PATENT DOCUMENTS

| | | |
|---|---|---|
| 48-376 | 1/1973 | Japan . |
| 910353 | 3/1982 | U.S.S.R. . |

OTHER PUBLICATIONS

Powers et al., *A New System of Field Shaping for External Beam Radiation Therapy*, Theraputic Radiology, vol. 108, pp. 407–411, Aug. 1973.
Luk et al., *Individualized Low-Melting Alloy Shielding Blocks for External-Beam Radiation Therapy*, Applied Radiology, Nov./Dec. 1977.
HUESTIS Styro–former brochure, Mar. 1993.

*Primary Examiner*—S. Thomas Hughes

[57] ABSTRACT

A method is described for indexing a polyfoam block in which a metal field shaping block is cast to both the cutting tray of a hot wire cutting system and the treatment tray of a radiation therapy treatment machine. The cast metal field shaping block is automatically correctly oriented for treatment. A cooling tray for cooling the casting is also described.

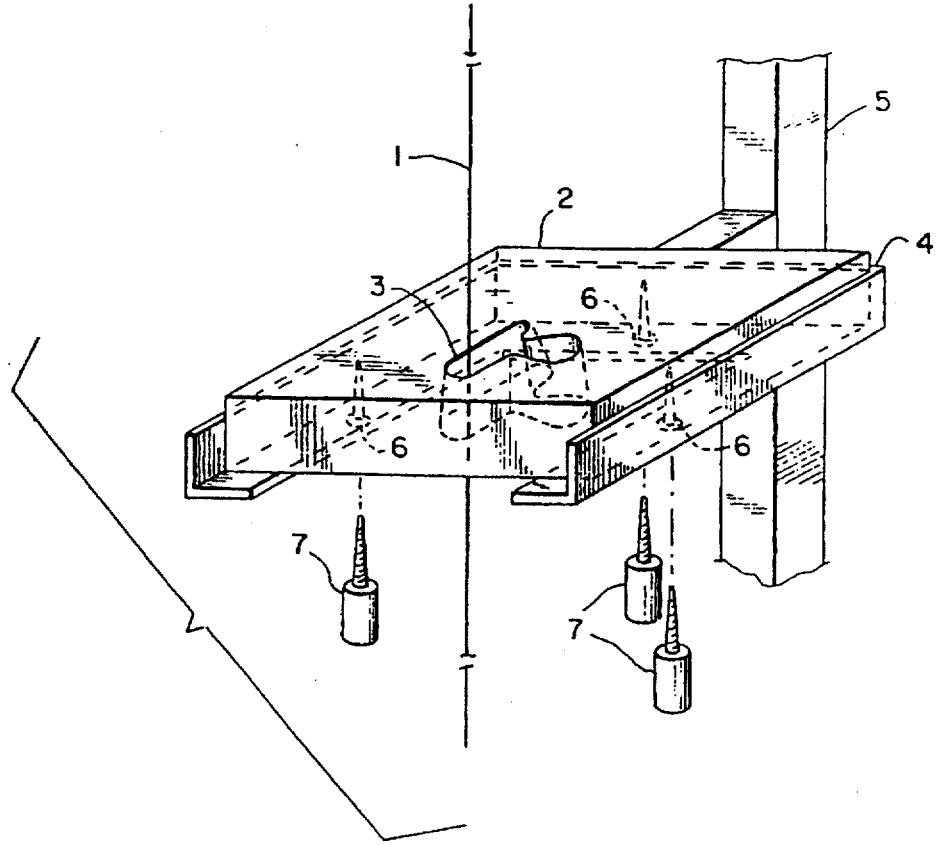

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–5 is confirmed.

* * * * *